United States Patent
Maeda

(10) Patent No.: US 7,219,566 B1
(45) Date of Patent: May 22, 2007

(54) AUTOMATIC SAMPLER

(75) Inventor: Yoshiaki Maeda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 11/260,635

(22) Filed: Oct. 28, 2005

(51) Int. Cl.
*G01N 1/22* (2006.01)
*B01L 3/02* (2006.01)

(52) U.S. Cl. ..................................... 73/864; 73/864.01
(58) Field of Classification Search ............. 73/863.01, 73/864.01, 864.21, 864; 436/43; 422/100
See application file for complete search history.

(56) References Cited

U.S. PATENT DOCUMENTS 4,944,781 A * 7/1990 Ruggirello et al. ........ 73/23.41
5,770,272 A * 6/1998 Biemann et al. ............ 427/162
2002/0102185 A1* 8/2002 Tatsumi ...................... 422/100

* cited by examiner

*Primary Examiner*—Hezron Williams
*Assistant Examiner*—Tamiko Bellamy
(74) *Attorney, Agent, or Firm*—Manabu Kanesaka

(57) ABSTRACT

An automatic sampler for automatically sampling liquid samples to be introduced into apparatuses that analyze liquid samples, such as liquid chromatographs, includes a needle with a tapered tip end for suctioning and ejecting liquid, a mechanism for moving the needle in the horizontal and vertical directions, and an injection port having an insertion hole into which the tip end of the needle can be inserted. The outer diameter of the tip end of the needle is at least 0.1 mm and at most 0.6 mm. By reducing the needle-to-port contact area, the automatic sampler facilitates high-sensitivity and high-precision analyses by significantly reducing the amount of cross-contamination, regardless of the type of samples.

5 Claims, 5 Drawing Sheets

US 7,219,566 B1

AUTOMATIC SAMPLER

BACKGROUND OF THE INVENTION AND RELATED ART STATEMENT

The present invention relates to automatic samplers for automatically sampling liquid samples to be introduced into analytical apparatuses that analyze liquid samples, such as liquid chromatographs.

In a liquid chromatograph, an automatic sampler is used in order to automatically select numerous samples to be introduced to columns. FIG. 3 is a schematic diagram showing the channel structure of a conventional automatic sampler used in a liquid chromatograph, as shown in Patent Reference 1.

In the automatic sampler 3, the injection valve (high-pressure valve) 4 is a rotary six-port, two-position channel switching valve having six ports 4a–4f. Through a switching operation, two adjacent ports are selectively connected. In other words, the combinations of the two-port connections indicated by the solid or broken lines in FIG. 3 can be switched. The low-pressure valve 5 is a rotary seven-port, six-position valve having seven ports 5a–5g. The common port 5g, which is connected to a measuring pump 6, can be coupled to any one of the other six ports 5a–5f, which accordingly couples two predetermined adjacent ports among ports 5a–5f. For example, when the common port 5g is coupled to port 5b, ports 5a and 5f are coupled, as indicated by solid lines in FIG. 3.

A column channel, which extends to column 2, is connected to port 4b of the injection valve 4, and a mobile phase channel, which is supplied with a mobile phase (solvent) by the liquid feeding unit 1, is connected to port 4c. A sample loop 7 is connected to port 4d, and also to port 4a via the needle 10 and the injection port 9. Ports 4e and 4f are connected to ports 5b and 5c of the low-pressure valve 5, respectively. A cleaning port 8 is connected to port 5a of the low-pressure valve 5, port 5e is connected to the measuring pump 6, and a cleaning solution is supplied to port 5d. A small vial 11 containing a liquid sample is stored in a sample rack 12. The needle 10 is moved in horizontal and vertical directions using a moving mechanism 13. The needle can be moved to locations above the vial 11 and the cleaning port 8, and inserted into the respective liquids contained therein.

The basic sequence of operations for introducing a liquid sample in the apparatus described above will be explained. When the liquid sample is collected, the injection valve 4 and the low-pressure valve 5 are switched to the connected state indicated by the solid lines in FIG. 3, and the needle 10 is moved to the location above the vial 11 and inserted into the liquid sample (the position indicated by reference numeral 10'). When the plunger of the measuring pump 6 is pulled in this state, the liquid sample is suctioned from the vial 11 through the mobile phase (or a cleaning solution made of the same components) that fills the connecting channel between the measuring pump 6 and the needle 10, and the liquid sample is held within the sample loop 7. The amount of the liquid sample collected is equivalent to the amount of suction developed by the measuring pump 6.

After the sample is collected, the needle 10 is returned to the position above the injection port 9 and connected to the injection port 9. The injection valve 4 is switched to the connected state indicated by the broken lines in FIG. 3. The mobile phase supplied from the liquid feeding unit 1 is transmitted to the column 2 via the sample loop 7, needle 10, and injection port 9. At this point, the liquid sample, which has been held within the sample loop 7, is fed to the column 2 along with the mobile phase. The liquid is separated into components as it passes through the column 2 to be sequentially detected by the detector, which is not shown.

The needle 10 on which the liquid sample is deposited during the suction is cleaned as follows. The injection valve 4 and the low-pressure valve 5 are switched to the connected state indicated by the solid lines in FIG. 4. The plunger of the measuring pump 6 is pulled to suction the cleaning solution into the syringe. When the injection valve 4 and the low-pressure valve 5 are subsequently switched to the connected state indicated by the broken lines in FIG. 3, and the plunger is pressed to eject the cleaning solution from the measuring pump 6, the cleaning solution is introduced to fill the cleaning port 8, while discharging excess cleaning solution from the discharge port of the cleaning port 8. The needle 10 is then moved to the location above the cleaning port 8, as shown in FIG. 4, and dipped into the cleaning solution contained in the cleaning port 8. Upon cleaning the needle 10 for a certain period of time, the needle is returned to the injection port 9.

In the aforementioned automatic sampler 3, since the cleaning of the needle 10 described above is always performed between the introductions of one liquid sample and the next, the likelihood of cross-contamination, wherein the previous sample is mixed into the following sample, is reduced. However, even with such cleaning steps, cross-contamination is not completely eliminated. One reason for that is explained below.

FIG. 5 is an enlarged schematic longitudinal sectional view of the section where the needle 10 comes in contact with the injection port 9. The section indicated as "A" of the needle 10 is straight, and the section indicated as "B" is tapered so that the outer diameter thereof is continuously reduced towards its tip. The sealing member 90 disposed in the injection port 9 is provided with an insertion hole 90b with a wider funnel section 90a. To connect the needle 10 to the injection port 9, the needle 10 is lowered so that the tip end of the needle 10 is inserted into the insertion hole 90b of the sealing member 90.

Since the inner diameter of the insertion hole 90b is larger than the outer diameter of the tip end of the needle 10, the tip end of the needle 10 begins entering the insertion hole 90b. Since the tip section of the needle 10 is tapered, the outer surface of the needle 10 comes in contact with the inner surface of the insertion hole 90b when the needle 10 is lowered to a certain position. The needle 10 is lowered by a predetermined level of pressure; the needle 10 is pushed in while the pressure overcomes the frictional force (including the resilience of the sealing member 90) of the contact surface, but the lowering of the needle 10 ceases once the frictional force surpasses the pressure. In other words, at this point, the outer surface of the needle 10 is in tight contact with the inner surface of the insertion hole 90b, thereby securing fluid-tightness.

When a liquid sample is suctioned from the vial 11, some of the liquid sample is deposited on the outer part of the tip end of the needle 10. The needle 10 is subsequently inserted into the sealing member 90 of the injection port 9 as above, and thus the liquid sample gets deposited on the section of the inner surface of the insertion hole 90b of the sealing member 90 where the outer surface of the tip of the needle 10 comes in contact. The liquid sample adhering to the contact surface is not removed even when the mobile phase is supplied from the needle 10 to the injection port 9, and thus remains even after the removal of the needle 10. When the needle 10 is inserted into the insertion hole 90b of the sealing member 90 in order to introduce the next liquid sample, the previous liquid sample adhering to the inner surface of the insertion hole 90b may be pushed by the needle 10 and mixed in the channel.

Such cross-contamination described above often causes problems, particularly in analyzing samples that are easily adsorbed by the surface of a needle 10 made of metal, such as basic compounds and lipid soluble substances.

Conventionally, for example, as in the automatic sampler disclosed in Patent Reference 2, a vapor-deposit or coating of precious metal is applied to the outer surface of the tip section of the needle in order to make the chemical adsorption of samples more difficult. Such a technique may be effective for samples that adhere to the needle surface mainly through chemical adsorption, such as basic compounds, but is not effective for samples that adhere to the needle surface through causes other than chemical adsorption, such as with lipid soluble substances.

Patent Reference 1: Japanese Laid-open Patent Publication No. 2002-277450

Patent Reference 2: Japanese Laid-open Patent Publication No. 2002-228668

In recent years, with increased levels of sensitivity and precision of analytical apparatuses, even a trace amount of cross-contamination such as that described above has begun to greatly affect the results of analyses. Moreover, samples that are subject to analysis have also diversified. A need exists for a cross-contamination reduction measure that does not depend on the type of samples.

An object of the present invention is to solve the aforementioned problems associated with conventional sampling devices. It is an object of the present invention, therefore, to provide an automatic sampler that enables high-sensitivity and high-precision analyses by significantly reducing the amount of cross-contamination, regardless of the type of samples.

While in the aforementioned conventional approach, the surface of a needle is designed so as to make adhesion of samples more difficult, the present invention addresses the fact that the amount of cross-contamination greatly depends on the contact area between the outer surface of the needle tip and the inner surface of the injection port's insertion hole. The present invention, therefore, is based on reducing the amount of cross-contamination by reducing the contact area.

Further objects and advantages of the invention will be apparent from the following description of the invention and the associated drawings.

SUMMARY OF THE INVENTION

The present invention achieves the aforementioned objects by providing an automatic sampler that includes a needle with a tapered tip end for suctioning and ejecting liquid, a mechanism for moving the needle in the horizontal and vertical directions, and an injection port having an insertion hole into which the tip end of the needle can be inserted. The automatic sampler introduces a liquid sample into an analysis channel by dipping the tip end of the needle into a liquid sample stored in a container to suction and hold the liquid sample in a retention channel via the needle, and then inserting the tip end of the needle into the insertion hole of the injection port to eject the liquid sample previously retained. The outer diameter of the tip end of the needle is at most 0.6 mm, and at least 0.1 mm.

Conventionally, the outer diameter of the tip end of a conventional needle has been 0.65 mm or larger. In the automatic sampler according to the present invention, however, the outer diameter of the tip end of the needle is smaller, i.e., 0.6 mm at most, and 0.1 mm at the least. Thus, the contact area between the outer surface of the needle tip, which is inserted into the injection port's insertion hole, and the inner surface of the injection port's insertion hole is reduced. This reduces the absolute amount of the liquid sample transferred from the outer surface of the needle to the inner surface of the injection port's insertion hole, i.e., the amount adhering to the inner surface, when introducing the liquid sample via the injection port. As a result, the amount of cross-contamination can be reduced relative to that of a conventional automatic sampler.

For example, the automatic sampler of the present invention employed in a liquid chromatograph prevents the peak derived from a component in a previous sample from appearing in the chromatogram. Even if the peak did appear to some extent, the peak intensity would be reduced relative to that in a conventional sampler. This increases the accuracy in calculating peak heights and peak areas of object components, thereby improving the accuracy of analyses. In addition, components found only in trace amounts, which have been conventionally undetectable due to cross-contamination, can be detected, thereby improving analysis sensitivity.

When the outer diameter of the needle tip is reduced, however, its mechanical strength is also reduced, thereby rendering the needle susceptible to buckling or the like during insertion. In the automatic sampler in the present invention, therefore, it is preferable to reduce the pressure applied during the insertion of the needle into the injection port's insertion hole from the conventional 4 kg, to 3 kg or less.

The aforementioned reduction in the contact area between the outer surface of the needle tip and the inner surface of the injection port's insertion hole also reduces the frictional force experienced during the needle insertion. Thus, even when the pressure is reduced, the needle can be pressed into the insertion hole sufficiently deep enough to ensure fluid-tightness, thereby preventing buckling or deformation of the needle.

By maintaining the same tapering angle of the tip section itself as that of the conventional device, even when the outer diameter of the needle tip is reduced, the resisting force experienced during the insertion of the needle into the septum remains the same as in the conventional device; the initial penetration resistance is smaller in proportion to the reduced outer diameter.

DETAILED DESCRIPTION OF THE PREFERRED EMBODIMENTS

In the following description, embodiments of the present invention will be explained with reference to the associated drawings.

Figure 1A:
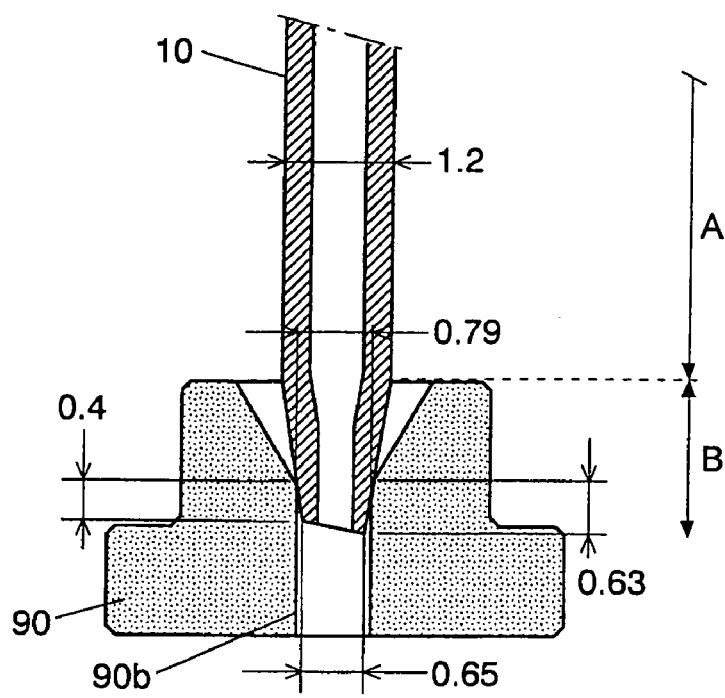
FIGS. 1(a) and 1(b) are longitudinal sectional views comparatively showing a section where a needle contacts an injection port in, respectively, a conventional automatic sampler (FIG. 1(a)), and an automatic sampler according to one embodiment of the present invention (FIG. 1(b)).
Figure 1B:
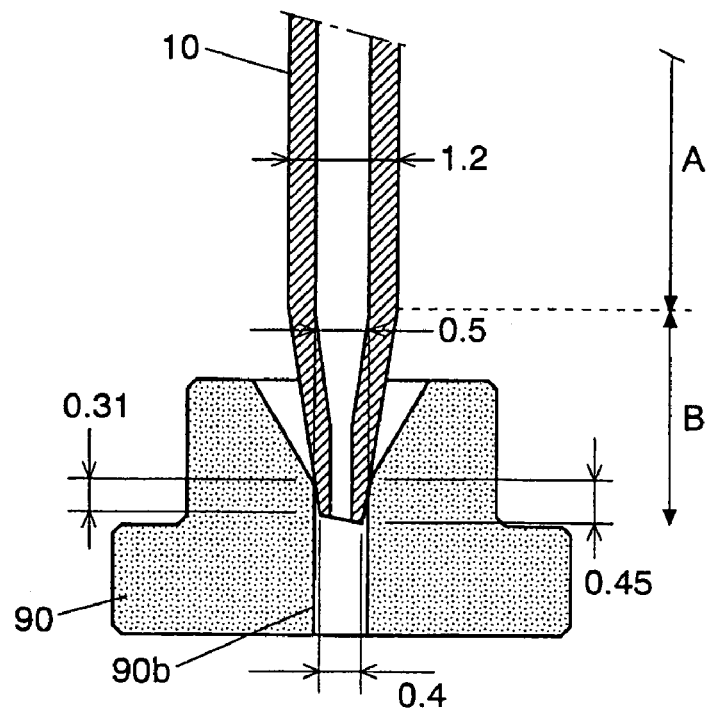

In the following, an automatic sampler according to one embodiment of the present invention will be explained with reference to FIGS. 1(a) and 1(b). FIGS. 1(a) and 1(b) are longitudinal sectional views showing the state where a needle 10 is inserted into an insertion hole 90b of a sealing member 90 of an injection port 9. FIG. 1(a) illustrates a conventional automatic sampler, and FIG. 1(b) illustrates an automatic sampler according to one embodiment of the present invention. In FIGS. 1(a) and 1(b), the dimensions are expressed in millimeters (mm).

The needle 10 and the sealing member 9 used in the conventional automatic sampler shown in FIG. 1(a) will be explained first. The outer and inner diameters of the straight section of the needle 10 indicated as "A" in FIG. 1(a) are 1.2 mm and 0.4 mm, respectively. The outer and inner diameters at the tip of the tapered section indicated as "B" are 0.65 mm and 0.26 mm, respectively. Although the outer diameter in the tapered section is gradually reduced towards the tip end, the inner diameter remains straight. The inner diameter of the insertion hole 90b of the sealing member 90 is 0.79 mm. When the needle 10 is inserted into the insertion hole 90b of the sealing member 90, the needle 10 is lowered vertically from above while applying a pressure of about 4 kg.

When inserted, the depth (i.e., length) of the contact area between the outer surface of the tip end of the needle 10 and the inner surface of the insertion hole 90b is, on average, from 0.4 mm at the shortest to 0.63 mm at the longest.

The material used for the needle 10 is stainless steel, and the material used for the sealing member 90 is a polyether ether ketone resin, such as the resin sold under the registered trademark PEEK. In this respect, the materials of the needle 10 and the sealing member 90 are the same for the embodiment of the present invention described below.

In the automatic sampler according to the present invention, however, while the outer and inner diameters of the straight section of the needle 10 indicated as "A" in FIG. 1(b) are 1.2 mm and 0.4 mm, respectively, the outer and inner diameters at the tip of the tapered section indicated as "B" are 0.4 mm and 0.2 mm, respectively. Since the tapering angle of the tapered section is the same as in the conventional device, the length of the tapered section itself is longer, as is evident when FIGS. 1(a) and (b) are compared.

In the present invention, the inner diameter of the insertion hole 90b of the sealing member 90 is 0.5 mm in response to the reduced outer diameter of the tip end of the needle 10. Since the tip end of the needle 10 of the present invention is narrower that that of a conventional tip, the mechanical strength of the tip is less. Thus, in the present invention, the pressure applied to lower the needle 10 into the insertion hole 90b of the sealing member 90 is set to about 2 kg, or about one half that of the conventional sampler pressure. If the pressure is reduced when the outer diameter of the tip end of the needle 10 remains the same, the insertion depth of the needle 10 would be insufficient. In this embodiment, however, the frictional force between the insertion hole 90b of the sealing member 90 and the needle 10 is less, because the outer diameter of the needle 10 is smaller. Thus, the reduced pressure can press the needle 10 deep enough to ensure the fluid-tightness of the contact section.

According to the present invention, the length of the contact area between the outer surface of the tip end of the needle 10 and the inner surface of the insertion hole 90b is, on average, from 0.31 mm at the shortest to 0.45 mm at the longest.

As described above, since in this embodiment of the present invention the outer diameter of the tip of the needle 10 is reduced, and the inner diameter of the insertion hole 90b of the injection port 9 is also reduced accordingly, the area where the two come into contact when the needle 10 is inserted is therefore smaller that that in a conventional apparatus. More specifically, the contact area associated with the present invention is about one half that of the conventional apparatus. Thus, the amount of a liquid sample adhering to the contact area is reduced, and, as a result, the amount of cross-contamination is reduced.

An example demonstrating the effect of cross-contamination reduction according to the present invention will be explained next. In this experiment, a sample made of strong basic chlorhexidine hydrochloride (12 mg/10 mL) diluted in the same solution as the mobile phase was analyzed in order to obtain the peak area α. The mobile phase only (blank sample) was consecutively analyzed in the same manner in order to calculate the peak area β of the peak appearing in the same retention time. The amount of cross-contamination is expressed as the ratio of the peak area β to peak area α.

Figure 2A:
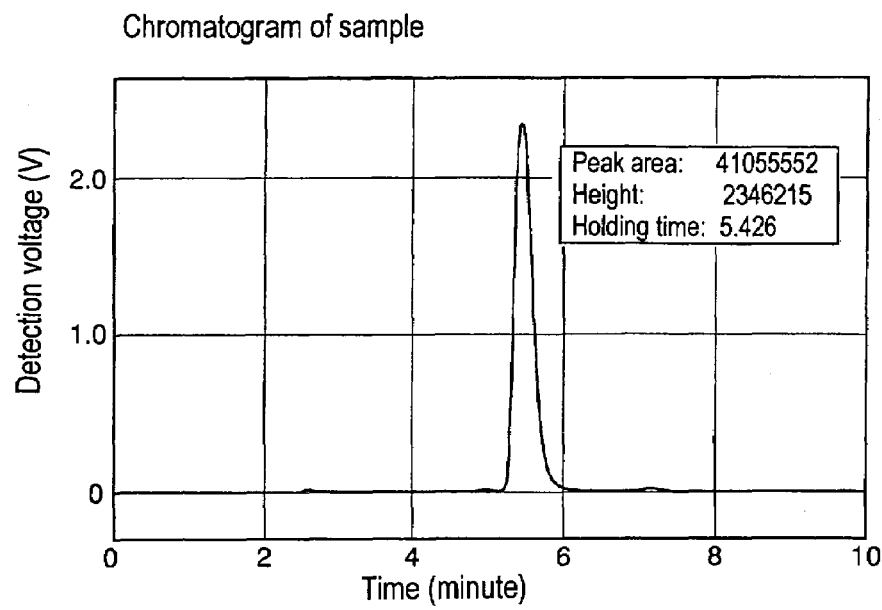
FIGS. 2(a) and 2(b) are charts for illustrating the effect of reducing cross-contamination achieved by the automatic sampler of the present invention.
Figure 2B:
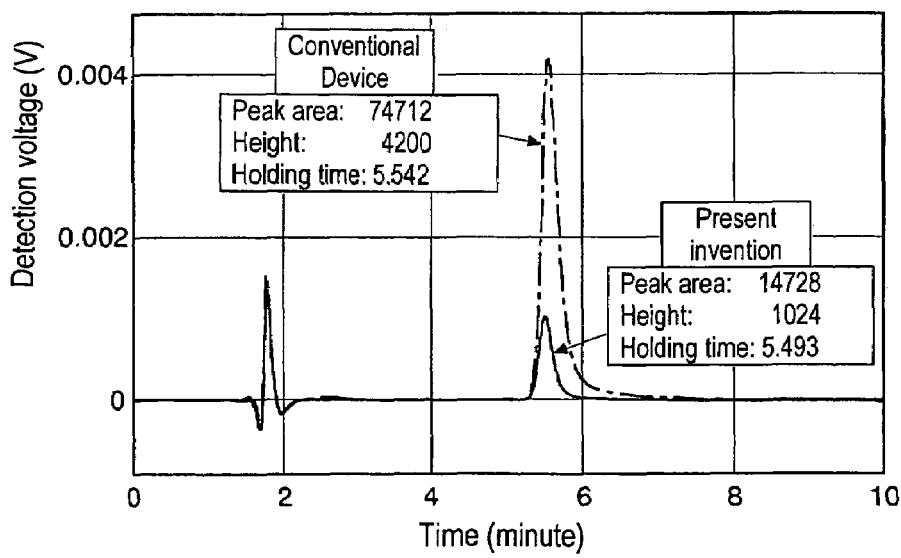
Figure 3:
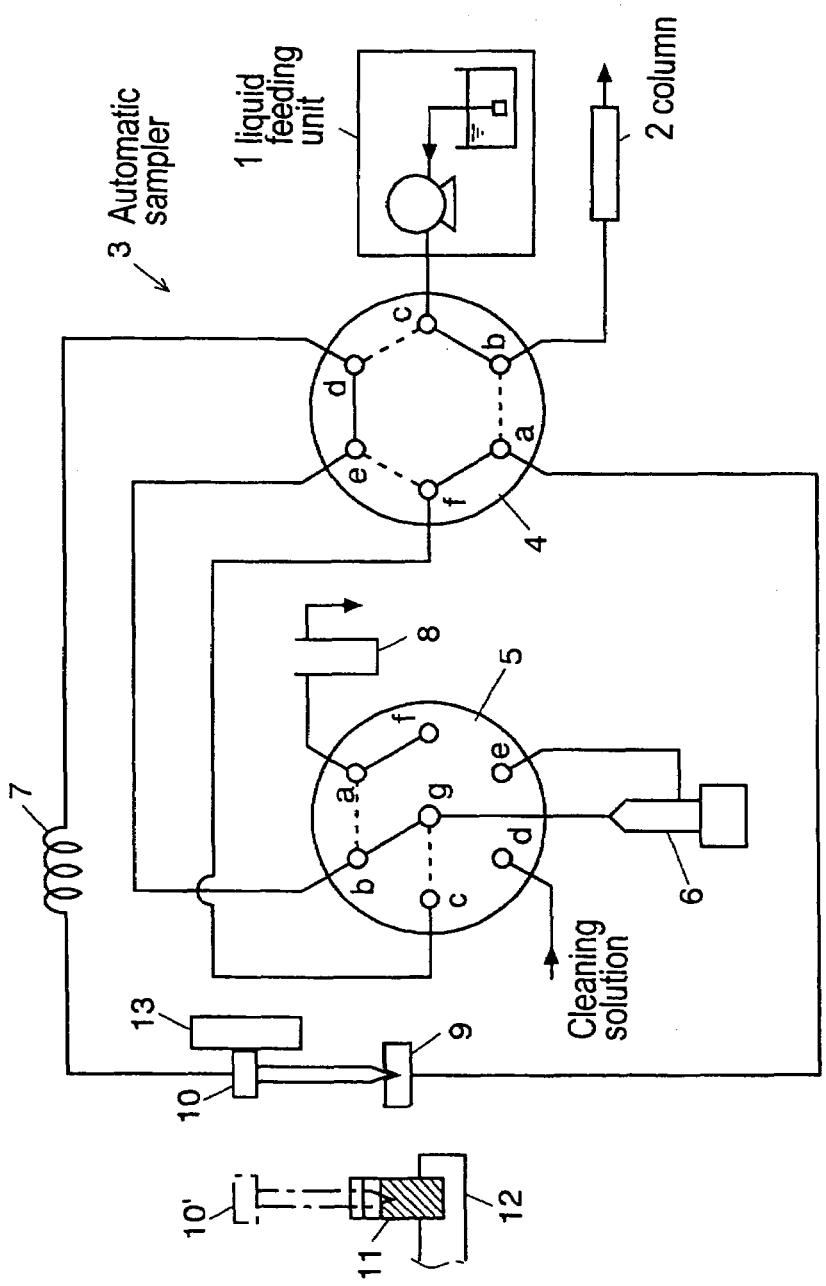
FIG. 3 is a first schematic diagram showing the channel structure of the conventional automatic sampler for a liquid chromatograph.
Figure 4:
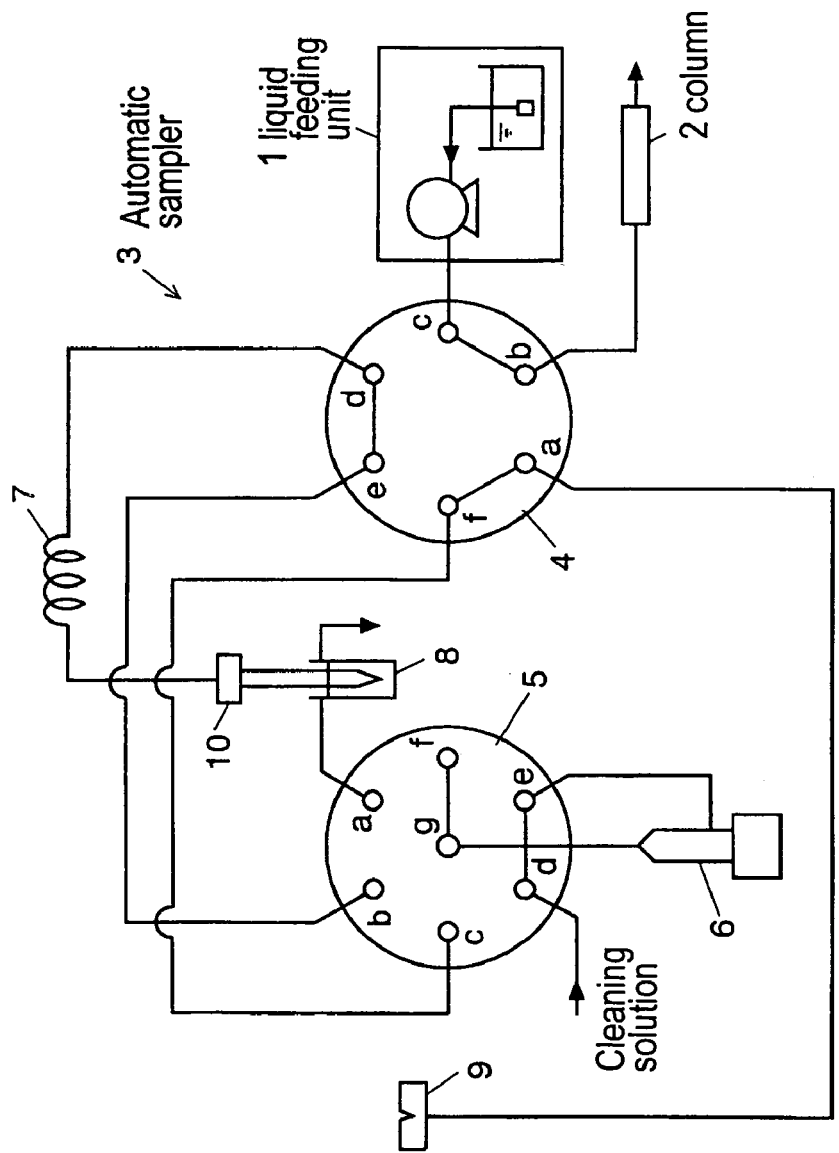
FIG. 4 is a second schematic diagram showing the channel structure of the conventional automatic sampler for a liquid chromatograph.
Figure 5:
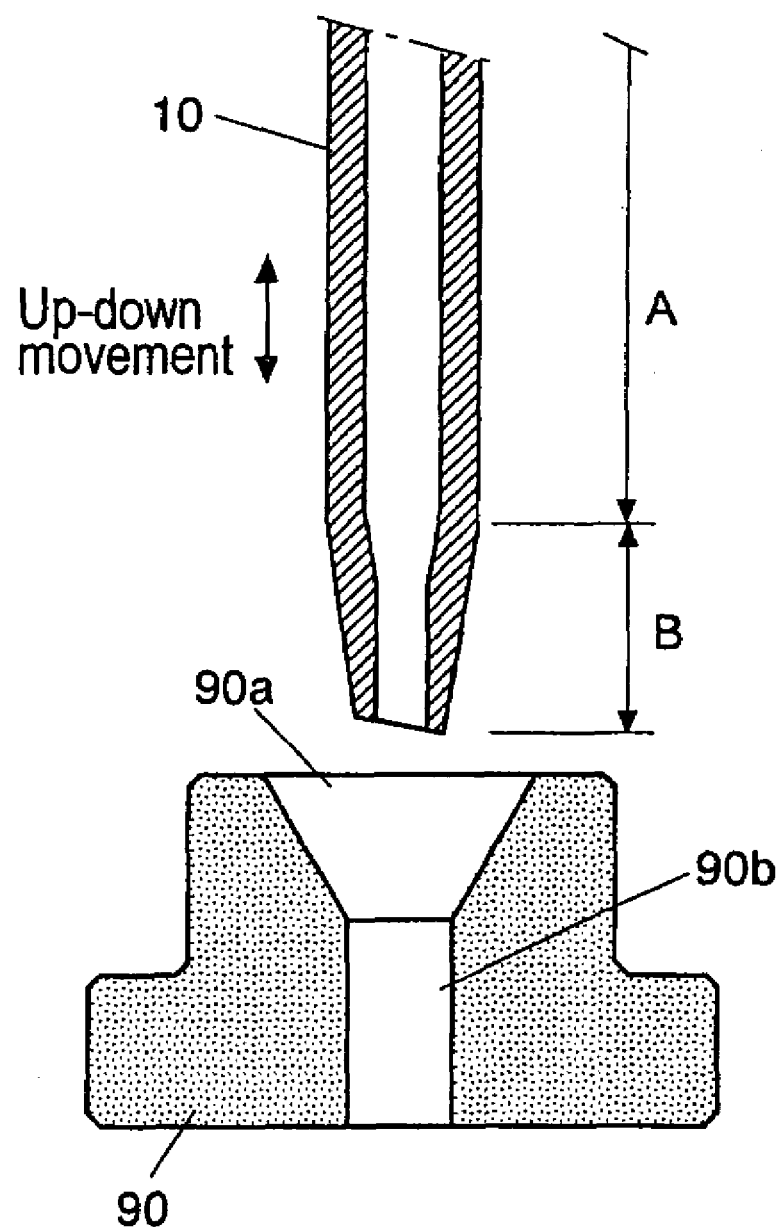
FIG. 5 is an enlarged longitudinal sectional view of connection sections of a needle and an injection port.

FIG. 2(a) is the resultant chromatogram of the aforementioned chlorhexidine hydrochloride solution, and FIG. 2(b) is the resultant chromatogram of the blank sample. On these charts, the graduations of the abscissas, which represent time, are the same, while the graduations of the ordinates, which represent intensity, are such that graduations in FIG. 2(b) are much smaller in scale than those of FIG. 2(a). The peak area α corresponding to chlorhexidine hydrochloride detected during the analysis of the sample obtained from FIG. 2(a) was 41055552. The peak area β corresponding to chlorhexidine hydrochloride detected during the analysis of the blank sample was 74712 for the conventional automatic sampler as opposed to 14728 for the automatic sampler of the present invention. The amounts of cross-contamination calculated from these values were 0.182% for the conventional automatic sampler and 0.036% for the automatic sampler of the present invention. In other words, the amount of cross-contamination in the automatic sampler of the present invention is reduced to about ⅕ that of the conventional automatic sampler.

The embodiment described above is merely one example of the present invention, and the dimensions for the outer diameter of the needle tip and the inner diameter of the sealing member's insertion hole are not necessarily limited to those disclosed. The outer diameter of the needle tip is, however, 0.6 mm at most. From the perspective of reducing contact area, it is desirable to reduce the outer diameter of the needle to the extent possible, but mechanical strength is reduced in proportion to the reduction in the outer diameter. Moreover, since a channel is formed inside the needle, reducing the channel's inner diameter too much would make it difficult to secure the necessary flow rate. Judging generally from these factors, the outer diameter of the needle tip needs to be at least 0.1 mm.

In addition, if the inner diameter of the sealing member's insertion hole is too small, the insertion of the tip of the needle 10 would be too shallow to ensure a sufficient level of fluid-tightness. If the inner diameter is too large, on the other hand, the insertion length of the tip of the needle 10 would be deep, and increase the contact area. Thus, the inner diameter must be set appropriately in correspondence with the outer diameter of the tip of the needle used.

The disclosure of Japanese Patent Application No. 2004-223321 is incorporated herein.

While the invention has been explained with reference to the specific embodiments of the invention, the explanation is illustrative and the invention is limited only by the appended claims.

What is claimed is:

1. An automatic sampler comprising:
   a container for storing a liquid sample;
   a needle having a tapered portion with a tip end for suctioning and ejecting the liquid sample, and a retention channel for holding said liquid sample suctioned from said container via said tip end, wherein an outer diameter of said tip end of said needle is at least 0.1 mm and at most 0.6 mm;
   a mechanism for moving said needle in a horizontal and a vertical direction;
   an injection port for receiving said held liquid sample, wherein said injection port has an insertion hole for insertably receiving said tip end of said needle and said liquid sample ejected therefrom, said insertion hole having a reduced contact area with an outer surface of the tip end of the needle; and
   an analysis channel connected to the injection port for receiving and analyzing said liquid sample,
   wherein said moving mechanism is arranged such that an insertion pressure applied when said tip end of said needle is inserted into said injection port is 3 kg or less.

2. The automatic sampler according to claim 1, wherein said insertion hole has an outer diameter greater than the outer diameter of said tip end and less than an outer diameter of a bottom of a tapered portion.

3. The automatic sampler according to claim 2, wherein said injection port has a tapered receiving portion and a straight portion extending from the receiving portion so that the tip end contacts the straight portion.

4. The automatic sampler according to claim 3, wherein said outer diameters of said tip end and said bottom are 0.4 mm and 1.2 mm, respectively, and a contacting length between the needle and the straight portion is about 0.45 mm.

5. The automatic sampler according to claim 4, wherein said insertion hole has a diameter of 0.5 mm, and the insertion pressure is about 2 kg.

* * * * *